United States Patent [19]

Harris et al.

[11] Patent Number: 5,103,026
[45] Date of Patent: Apr. 7, 1992

[54] PROCESS FOR PREPARING FURAN COMPOSITIONS

[75] Inventors: Eugene Harris, West Chester; Thomas Korte, Cincinnati, both of Ohio

[73] Assignee: Henkel Corporation, Ambler, Pa.

[21] Appl. No.: 513,139

[22] Filed: Apr. 23, 1990

[51] Int. Cl.$^5$ ............................................ C07D 307/32
[52] U.S. Cl. .................................... 549/486; 549/484
[58] Field of Search ................... 549/484, 486; 512/12

[56] References Cited

U.S. PATENT DOCUMENTS 4,681,703  7/1987  Harris et al. .......................... 512/11

FOREIGN PATENT DOCUMENTS 0128584  12/1984  European Pat. Off. .

OTHER PUBLICATIONS

Chemical Abstract 99:158162h p. 593 (1983).
Journal of Organic Chemistry, vol. 52, 1987, American Chemical Society (U.S.), T. Hosokawa et al., "Palladium(II)-Catalyzed Acetalization of Terminal Olefins Bearing Electron-Withdrawing Substituents . . . Diols", pp. 1758-1764.
Julius Grant, Hackh's Chemical Dictionary Fourth Edition, p. 101.
Korte et al., *Chemische Benichte*, 90, 2137-2149, (1957).
Korte et al., *Angewante Chemie*, No. 23, pp. 709-752, (1959).
Green, "Protective Groups in Organic Synthesis", pp. 114-129, John Wiley & Sons, New York (1981).

*Primary Examiner*—Glennon H. Hollrah
*Assistant Examiner*—Mark W. Russell
*Attorney, Agent, or Firm*—Ernest G. Szoke; Wayne C. Jaeschke; Daniel S. Ortiz

[57] ABSTRACT

A process for preparing a composition of the formula

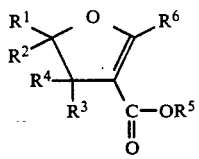
(I)

by reacting a composition of the formula

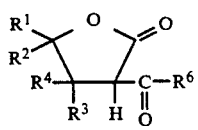
(IV)

with a polyhydric alcohol of the formula HO—X—OH in the presence of an acid catalyst at an elevated temperature to form a ketal of the formula

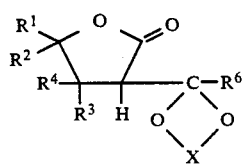
(II)

and reacting the ketal of the formula (II) with a monohydric alcohol in the presence of an acid at an elevated temperature to form

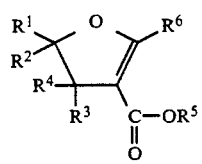
(I)

11 Claims, No Drawings

PROCESS FOR PREPARING FURAN COMPOSITIONS

FIELD OF THE INVENTION

The invention is a process for preparing compositions of the formula

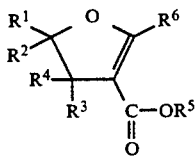

(I)

wherein $R^1$, $R^2$, $R^3$, $R^4$, $R^5$, and $R^6$ are as defined below and certain novel intermediate compositions.

RELATED ART

Compositions of the formula (I) have been made by reacting a monohydric alcohol with a furanone of the formula

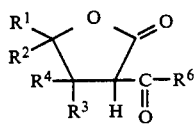

(IV)

under acidic conditions and an elevated temperature. The yield of the composition (I) is low due to hydrolysis and the formation of by-products. Furanones of the formula IV are known compositions. Processes for preparing these compositions are disclosed in Chemische Berichte 90:2137-2149 (1957) and Angewandte Chemie No. 23, pgs. 709-752 (Dec. 7, 1959). The processes disclosed in the references provide low yields of the desired materials unless a large excess of the alcohol is utilized. The present invention provides a process in which compositions (I) can be prepared in high yields without use of a large excess of alcohol.

BRIEF DESCRIPTION OF THE INVENTION

According to the present invention, a process and novel intermediate compositions, prepared by the process, are provided to prepare compositions of the formula (I). According to the present invention, compositions of the formula

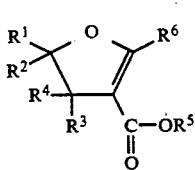

(I)

wherein $R^1$, $R^2$, $R^3$, $R^4$, and $R^6$ are each independently hydrogen, alkenyl having from 2 to about 20 carbon atoms which can be substituted with halo, lower alkoxy and aryl, alkyl each having from 1 to about 20 carbon atoms which can be substituted with halo, lower alkoxy and aryl, cycloalkyl having from 5 to about 20 carbon atoms which can be substituted with lower alkyl, lower alkoxy, lower alkoxyalkyl and halo, aryl having from 6 to about 20 carbon atoms which can be substituted with lower alkyl, lower alkoxy, lower alkoxyalkyl and halo; cycloalkenyl having from about 5 to about 20 carbon atoms which can be substituted with lower alkyl, lower alkoxy, lower alkoxyalkyl and halo; and wherein $R^5$ can be alkenyl having from 2 to about 20 carbon atoms which can be substituted with halo, lower alkoxy and aryl, alkyl having from about 1 to about 20 carbon atoms which can be substituted with halo lower alkoxy and aryl; cycloalkyl having from 5 to about 20 carbon atoms which can be substituted with lower alkyl, lower alkoxy, lower alkoxyalkyl and halo, aryl having from 6 to about 20 carbon atoms which can be substituted with lower alkyl, lower alkoxy, lower alkoxyalkyl and halo, and cycloalkenyl having from 5 to about 20 carbon atoms which can be substituted with lower alkyl, lower alkoxy, lower alkoxyalkyl, and halo are prepared by a process which comprises: reacting a composition of the formula

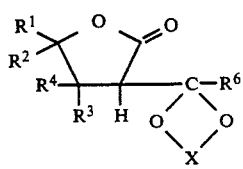

(II)

wherein X is the residue of a polyhydric organic composition having at least two hydroxyl groups in a spatial relation sufficiently close to permit them to react with the furanone to form a compound of the formula (II); with an alcohol of the formula $R^5OH$, wherein $R^5$ is as defined above, in the presence of a catalytic amount of an acid having a $pK_8$ of from about 2 to $-12$ and at a temperature effective to form the composition (I).

The present invention also encompasses a process wherein a ketal of the formula:

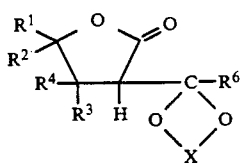

(II)

is formed by a process which comprises:
1) forming a mixture comprising:
   a) a composition of the formula

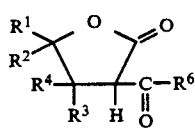

(IV)

b) at least a stoichiometric amount of a composition of the formula

HO—X—OH  (III)

to form a ketal, wherein X and $R^1$, $R^2$, $R^3$, $R^4$, and $R^6$ are as defined above:
c) an azeotropic agent for the removal of water;
d) a catalytic effective amount of an acid having pKa of from about 4 to about $-12$; and
2) heating the mixture to a temperature effective to react (a) with (b) with the azeotropic removal of water to form the ketal

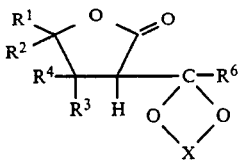

The invention also encompasses novel compositions of the formula

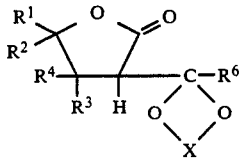

DETAILED DESCRIPTION OF THE INVENTION

Throughout the specification, composition of formula (I) refers to

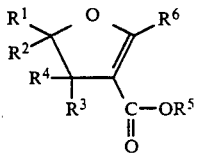

composition of formula (II) refers to

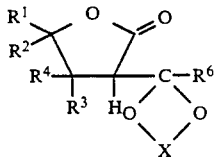

composition of formula (III) refers to

HO—X—OH composition of formula (IV) refers to

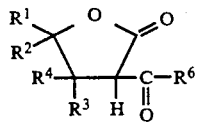

The compositions of the formula

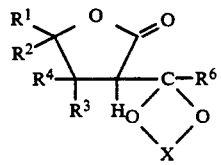

are novel compounds. The moieties $R^1$, $R^2$, $R^3$, $R^4$, $R^6$ and X are as defined above. Preferably, $R^1$ and $R^6$ are alkyl having from 1 to about 6 carbon atoms and $R^2$, $R^3$, and $R^4$ are hydrogen.

X is the residue of a polyhydric organic composition having at least two hydroxyl groups in a spatial relation sufficiently close to permit them to react with the furanone to form a composition of the formula (II)

X includes residues of dihydric and polyhydric organic compositions of the formula

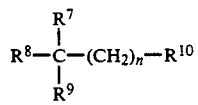

wherein $R^7$, $R^8$, $R^9$ and $R^{10}$ are each independently hydrogen, alkyl having from 1 to about 10 carbon atoms, OH, or hydroxyalkyl having from 1 to about 10 carbon atoms and n is 0, 1 or 2. $R^7$, $R^8$, $R^9$ and $R^{10}$ together contain at least two OH group. $R^{10}$ can be alkyl or -CHOH which is joined with $R^9$ to form a ring with the number of carbon atoms in $R^9$ being from 3 to 10, $R^9$ being an alkyl or hydroxyalkyl, n is zero and the compound having at least two hydroxyl groups in a spatial relation to permit a ketal to form.

Useful polyhydric organic compositions include compounds such as glycerine, polyglycerine containing up to about 4 glycerol residues, trimethylol propane, pentaerythritol, cyclodecane 1,2 diol and cyclododecane 1, 2 diol.

Preferred polyhydric compounds include compounds such as 1, 2-hexanediol, 1, 2-pentanediol, 1, 2-butanediol, 1, 3-butanediol, 1, 3-propanediol, 1, 2-propanediol, ethylene glycol, glycerine, trimethylolpropane, cyclohexane 1, 2-diol, cyclopentane 1,2-diol, cyclooctane 1, 2-diol and the like.

Compositions of the formula

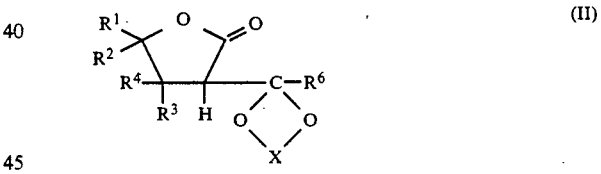

are prepared by reacting a furanone of the formula

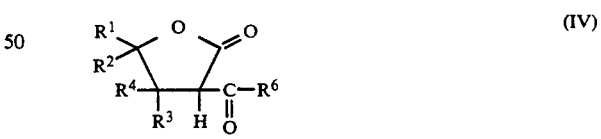

with a composition of the formula

HO—X—OH (III)

in the presence of an azeotropic agent and an acid catalyst at an elevated temperature sufficient to azeotropically remove the water formed during the reaction substantially as soon as it is formed. The reaction mixture is preferably anhydrous or as low in water content as can be maintained by the continued azeotropic removal of the water formed during the reaction between the compound of the formula HO—X—OH (III) with a compound of the formula;

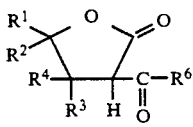

(IV)

$R^1$, $R^2$, $R^3$, $R^4$, $R^6$, X are as defined above.

Preparation of the composition of the formula (II) is preferably carried out by reaction in the presence of a relatively weak acid catalyst having a PKa, in relation to water, of from about 4 to about −12, preferably from about 4 to about −6 and more preferably from about 2 to −6. The process is operated so that a composition of the formula (II) is formed without substantial amounts of a transesterification or hydrolysis reaction taking place. This can be accomplished by utilizing a relatively weak acid such as alkali metal bisulfates ($HSO_4^-$), oxalic acid and the like, at an elevated temperature in a reaction mixture containing low amounts of water. The amount of hydrolysis and transesterification can be controlled by the proper selection of the azeotropic agent, the catalyst, the amount of catalyst and the reaction temperature.

Utilizing relatively weak acids such as alkali metal bisulfates, oxalic acid, alkali metal dihydrogen phosphates and the like and a properly selected azeotropic agent, the process can be operated at temperatures in the range of about 50° C. to about 150° C. and preferably from about 80° to about 130° C. without substantial transesterification and hydrolysis of the reaction product to undesired by-products. The elevated temperature provides for the selection of an azeotropic agent such as toluene or xylene which can remove the water formed in the process at a temperature at which the water has a relatively high vapor pressure and only relatively small quantities remain in the reaction mixture.

If stronger acidic catalyst such as hydrogen chloride, sulfuric acid, nitric acid, p-toluene sulfonic acid and the like are utilized as the acid catalyst in forming the composition of formula (II), lower temperatures must be utilized and azeotropic agents having a lower boiling point such as pentane, hexane or benzene must be utilized.

When utilizing acids such as sulfuric acid or hydrochloric acid, the process for preparing compounds of the formula (II) should be operated in the range of below about 60° C. Use of weaker acids as catalysts is preferred so that the process for forming (II) can be carried out at an elevated temperature to ensure rapid removal of the water formed by the reaction.

Generally, the acid catalyst is present in the range of from about 0.1 to about 15 percent by weight and preferably from about 0.5 to about 5 percent by weight of the furanone compound.

The azeotropic agent utilized in the process is a composition which does not react in the process and is generally a hydrocarbon composition such as pentane, hexane, heptane, octane, benzene, toluene, xylene, ethylbenzenes, cyclohexane, methyl cyclohexane, ethyl cyclohexane and the like.

During the process of reacting the composition of the formula (IV) with the composition of formula (III) in the presence of the acid catalyst and the azeotropic agent to form the composition of the formula (II), the azeotropic agent is maintained at its boiling point so that the water formed, by the reaction of (IV) with (III), is removed from the reaction system to reduce the tendency for hydrolysis to occur. In addition, removal of the water formed in the reaction, shifts the equilibrium toward formation of the compound (II) the desired product.

The composition of the formula (II) is then reacted with an alcohol of the formula $R^5OH$ in the presence of an acid catalyst to form a composition of the formula (I). The composition of the formula (II) can be separated from the azeotropic agent before the addition of the alcohol of the formula $R^5OH$ or the azeotropic agent can remain in admixture with the composition (II).

The reaction between the compound of the formula (II) and the alcohol $R^5OH$ is carried out in the presence of a strong acid catalyst at a temperature in the range of from about 70° C. to about 150° C. preferably about 90° C. to about 130° C. If the alcohol has a sufficiently high boiling point, the reaction can be carried out at atmospheric pressure. However, if a more rapid reaction is required and the alcohol has a boiling point below the desired reaction temperature, the reaction system can be reacted at an elevated pressure to substantially reduce the reaction time. Since there is substantially no water present in the reaction mixture, the use of the strong acid catalyst and the elevated temperature does not produce hydrolysis and substantial amounts of unwanted by-products. The yield based on the amount of composition of the formula (II) is high. The amount of alcohol used in the process can be in the range of about 1:1 to about 10:1 and preferably from about 3:1 to about 5:1 mols of monohydric alcohol per mol of ketal (II).

After the reaction between the compound of the formula (II) with the alcohol which is preferably present in stoichiometric excess, the reaction mixture is neutralized with an alkaline material, the materials more volatile than the desired product (I) are removed from the reaction mixture under a reduced pressure, the remaining material is then contacted with alkaline, neutral or acid water wash solutions, the material dried and if further purification is desired the composition of the formula (I) can be recovered by distillation, crystallization or other methods known for purifying organic compounds.

As used herein, stoichiometric excess denotes an amount of material in excess of the amount theoretically required to react all (100%) of a material to the desired reaction product.

During the process for preparing compounds of the formula (I) or (II), the progress of the reaction can be followed by periodic sampling of the reaction mixture and analysis by gas chromatography or other methods known for rapidly analyzing organic mixtures. The process of the present invention will be illustrated by the following examples.

Certain compositions of the formula (I) are fragrance and aroma compositions which have utility in providing fragrance values to commercial compositions and as intermediates.

COMPARATIVE EXAMPLE 1

This example illustrates the prior art process for preparing compounds of the formula (I).

A reaction mixture comprising 83.5 grams of 3-acetyl-5-butyl-dihydro-2(3H)-furanone, 100 grams of anhydrous ethanol and 0.5 grams of concentrated sulfuric acid were refluxed for 6 hours. After 6 hours, the excess ethanol was removed under vacuum at a temperature up to about 69° C. The crude mixture was mixed with 100 milliliters of ether and washed three times with 2N KOH. The organic layer was separated and dried over sodium sulfate and stripped on a Rotovap to recover 77.6 grams crude material. The crude material was fractionated to provide 35.3 grams of 2-butyl-4-carbethoxy-5-methyl-2,3 dihydrofuran. The yield was 37.3 percent based on 85.2 percent conversion of the starting furanone. The comparative example was carried out at a mol ratio of ethanol to 3-acetyl-5-butyl-dihydro-2(3H)-furanone of 5:1.

COMPARATIVE EXAMPLE 2

A mixture containing 16.0 grams of 3-acetyl-5-methyl-dihydro-2(3H)-furanone, 150 grams of dry n-propyl alcohol and 0.2 grams of concentrated sulfuric acid were refluxed for six hours. The mixture was neutralized with 0.16 grams of NaOH and 2 grams of water. The excess alcohol and remaining water were stripped from the mixture in a Rotovap at full aspirator vacuum to a temperature of 90° C. The residue was filtered through filter paper and fractionated to yield 15.6 grams of 2-methyl-4-carbpropoxy-5-methyl-2,3-dihydrofuran for a 76.2 percent yield based on a conversion of 94.0 percent of the starting furanone. The mol ratio of alcohol to furanone was 22.1:1.

The example shows that the yield of a dihydrofuran of the composition (I) can be substantially increased by utilizing a large excess of alcohol.

EXAMPLE 1

A mixture containing 750 grams of 3-acetyl-5-butyl-dihydro-2 (3H)-furanone (4.0 mols), 750 grams of cyclohexane and 8.6 grams of sodium hydrogen sulfate were heated to reflux. To the refluxing mixture were added 250 grams of ethylene glycol (4.0 mols) over a period of 6 hours while the water formed by the reaction was collected in a Dean Stark Trap. An additional 110 grams of ethylene glycol (1.8 mols) was added over 22 hours to replace glycol carried over with the refluxing cyclohexane (azeotropic agent). After 36 hours, an analysis of the reaction mixture showed that the furanone was 95.4 percent converted to a ketal of the formula

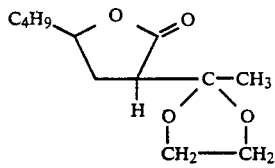

An aliquot of 94.5 grams of the mixture (0.22 mols) and 30.5 grams of anhydrous ethanol (0.66 mols) and 0.6 grams of p-toluene sulfonic acid were refluxed at 71° C. for 26 hours. The mixture was then neutralized with 0.73 grams of sodium ethoxide followed by stripping on a Rotovap under vacuum to a temperature of 90° C. The residue was water washed, dried on a Rotovap and distilled to provide 29.6 grams of 2-butyl-4-carbethoxy-5-methyl-2,3-dihydrofuran. The amount of recovered material represented a yield of 63.5 percent based on the amount of furanone reacted and a yield of 66.9% based on a 93.0% conversion of the ketal.

EXAMPLE 2

A mixture of 201.3 grams of crude 3-acetyl-5-propyl-dihydro-2 (3H)-furanone (1.18 mols), 90.0 grams of propylene glycol (1.18 mols), 50.3 grams of cyclohexane and 1.16 grams of sodium hydrogen sulfate were heated and refluxed for four hours. The water produced by reaction was collected in a Dean Stark trap. After refluxing for 4 hours, the cyclohexane was stripped from the reaction mixture at 80° C. and a vacuum which increased up to 20 inches vacuum. To the residue was added 271.4 grams of anhydrous ethanol (5.9 mols) and 2.8 grams of concentrated sulfuric acid. The mixture was heated to 110° C. in an autoclave for 2.5 hours. The mixture was cooled and neutralized with 2.6 grams of sodium hydroxide and stripped under 15 inches of vacuum at a temperature up to 100° C. The residue was washed with water and the organic layer separated and distilled to yield 150.2 grams of 2-propyl-4-carbethoxy-5-methyl-2,3-dihydrofuran for a yield of 64.3 percent based on a 92.8% conversion of the Ketal. As shown in the examples, the process of the present invention provides for a high yield of the dihydrofuran product without the use of large excesses of alcohol and the formation of large amounts of by-products formed by the processes of the prior art.

EXAMPLE 3

A one liter flask fitted with reflux condenser and a Dean-Stark trap was charged with 302.2 grams of 3-acetyl-5-butyl-dihydro-2(3H)-furanone (1.64 moles), 147.8 grams 2,3-butanediol (1.64 moles), 150 grams cyclohexane and 1.51 grams sodium hydrogen sulfate. The mixture was refluxed for 4.5 hours and the water of reaction collected in the Dean Stark trap. At the end of 4.5 hours the reaction mixture was analyzed and contained 1.2% by weight of the dihydrofuranone. A total of 543.7 grams of reaction mixture was obtained which contained 71.5% by weight of the reaction product (ketal) of the dihydrofuranone and the 2,3-butanediol. The yield was 92.6% ketal based on conversion of 98.8% of the starting dihydrofuranone.

An aliquot of 304.5 grams of the reaction mixture containing 71.5% ketal (0.85 moles) was mixed with 195 grams anhydrous ethanol (4.4 moles) and 1.1 grams concentrated sulfuric acid in a one liter autoclave. The mixture was heated at 110° C. for four (4) hours. After 4 hours the reaction mixture contained 3.7% by weight ketal. The reaction mixture was neutralized with 0.95 grams of sodium hydroxide, stripped on a Rotovap under full aspirator vacuum to a temperature of 90° C. to provide a crude material. The crude material was washed with 10% by weight of the crude of water. The organic layer was separated from the water phase, the organic layer was dried under vacuum and distilled to provide 133.9 grams of a product containing 97.0% by weight of 2-butyl-4-carbethoxy-5-methyl-2,3-dihydrofurane. The yield was 72.1% based on 96.3% conversion of the Ketal.

EXAMPLE 4

To a one liter flask fitted with thermometer, Dean Stark trap and condenser was added 92 gms. (0.5 moles) 9-acetyl-5-butyl-dihydro-2(3H)-furanone, 84 gms. (0.5 moles), transcyclooctanediol, 1.0 gm. sodium hydrogen sulfate and 200 gms. cyclohexane. The system was heated to reflux (80° C.) and after 2 hrs. 8.5 mls. of a water solution was collected in the Dean Stark trap. GC analysis indicated all the 3-acetyl-5-butyl-dihydro-2(3H)-furanone had reacted. The pot was stripped at a temperature up to 90° C. to remove the cyclohexane and after cooling 120 gms. (2.6 moles) anhydrous ethanol and 1.0 gm sulfuric acid was added to the flask. The mixture was than heated to relux for 48 hrs. at which time GC analysis showed an 8% conversion of the ketal to the desired 2-butyl-4-carbethoxy-5-methyl 1-2,3-dihydrofuran. The experiment was stopped at this point. It was clear that the material would have to be heated in a autoclove as in Example 3 at a temperature above 100°-110° C. and preferably about 100° C.-140° C. to increase the rate of formation of the furan compound.

As used herein lower alkyl, and lower alkoxy mean groups having from 1 to about 6 carbon atoms. Lower alkenyl refers to a group having from 2 to about 6 carbon atoms. Lower alkoxyalkyl refers to a group containing at least one alkoxy and at least one alkyl group wherein the alkoxy and alkyl groups contain from 1 to about 6 carbon atoms. Halo as used herein refers to fluorine, chlorine and bromine.

As can be seen from the examples, the process of the present invention provides a high yield of the desired furan compound without using large excesses of the reagents.

We claim:

1. A process for the preparation of a compound of the formula

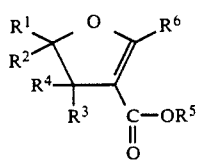

(I)

wherein $R^1$, $R^2$, $R^3$, $R^4$, and $R^6$ are each independently hydrogen, alkenyl having from 2 to about 20 carbon atoms which can be substituted with halo, lower alkoxy and aryl, alkyl having from 1 to about 20 carbon atoms which can be substituted with halo, lower alkoxy and aryl, cycloalkyl having from 5 to about 20 carbon atoms which can be substituted with lower alkyl, lower alkenyl, lower alkoxy, lower alkoxyalkyl and halo, aryl having from 6 to about 20 carbon atoms which can be substituted with lower alkyl, lower cycloalkyl, lower alkoxy, lower alkoxyalkyl and halo; cycloalkenyl having from 5 to about 20 carbon atoms which can be substituted with lower alkyl, lower alkoxy, lower alkoxyalkyl, and halo; and wherein $R^5$ can be alkenyl having from 2 to about 20 carbon atoms which can be substituted with halo, lower alkoxy, lower alkoxyalkyl and aryl, alkyl having from 1 to about 20 carbon atoms which can be substituted with halo, lower alkoxy, lower alkoxy alkyl and aryl, cycloalkyl having from 5 to 20 carbon atoms which can be substituted with lower alkenyl, lower alkyl, lower alkoxy, lower alkoxyalkyl, halo, and aryl, aryl having from 6 to about 20 carbon atoms which can be substituted with lower alkenyl, lower alkyl, lower alkoxy, lower alkoxyalkyl, and halo, cycloalkenyl having from 5 to about 20 carbon atoms which can be substituted with lower alkyl, lower alkoxy, lower alkoxyalkyl and halo; which comprises: reacting a compound of the formula

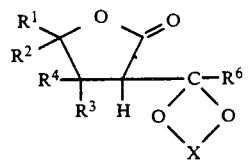

(II)

wherein X is a residue of a polyhydric organic compound having at least two hydroxy groups in a spatial relations sufficiently close to permit it to react with the furanone to form a compound of the formula (II), with an alcohol of the formula $R^5OH$ wherein $R^5$ is as defined above in the presence of a catalytic amount of an acid with a PKa of from about 2 to $-12$ and at a temperature effective to form the compound of the formula

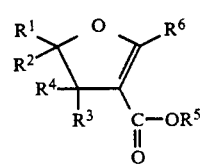

(I)

2. A process of claim 1 wherein $R^1$, $R^2$, $R^3$, $R^4$, and $R^6$ are each independently hydrogen or alkyl of from 1 to about 8 carbon atoms.

3. A process of claim 2 wherein $R^2$, $R^3$, and $R^4$ are each hydrogen.

4. A process of claim 3 wherein $R^1$, $R^5$, and $R^6$ are each independently alkyl from 1 to about 4 carbon atoms.

5. A process of claim 4 wherein X is $CH_2$—$CH_2$.

6. A process of claim 4 wherein X is $CH_2$—$CH$—$CH_3$.

7. A process of claim 4 wherein X is $H_3C$—$CH$—$CH$—$CH_3$.

8. A process of claim 1 which comprises:
1) forming a mixture comprising:
a) a compound of the formula

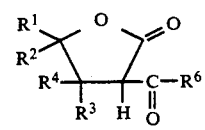

(IV)

b) at least a stoichiometric amount to form a Ketal, of a compound of the formula

HO—X—OH wherein X is the residue of a polyhydric organic compound of the formula

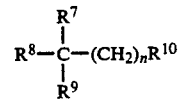

wherein $R^7$, $R^8$, $R^9$ and $R^{10}$ are each independently hydrogen, alkyl having from 1 to about 10 carbon atoms, OH, or hydroxyalkyl having from 1 to about 10 carbon atoms and n is 0, 1 or 2 and wherein $R^{10}$ can be alkyl or —CHOH which is joined with $R^9$ to form a ring with the number of carbon atoms in $R^9$ being from 3 to 10, $R^9$ being an alkyl or hydroxyalkyl and n is 0 and wherein the compound has at least two OH groups in a spatial relation to permit a Ketal to form;

c) an azeotropic agent for the removal of water;

d) a catalytic effective amount of an acid having a $pK_a$ of from about 4 to about $-12$; and 2) heating the mixture to a temperature effective to react a) with b) with the azeotropic removal of water to form a compound of the formula

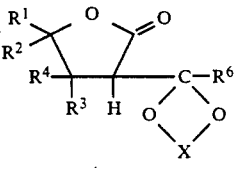

wherein $R^1$, $R^2$, $R^3$, $R^4$, $R^6$ are as defined in claim 1 and reacting the compound of the formula (II) in the process of claim 1.

9. A process of claim 8 wherein not more than one of $R^7$, $R^8$, $R^9$ or $R^{10}$ is alkyl.

10. A process of claim 8 wherein the azeotropic agent comprises at least one hydrocarbon selected from the group consisting of hexane, heptane, cyclohexane, benzene, toluene and xylene.

11. A process of claim 8 wherein the acid having a pKa of from about 4 to about $-12$ is selected from the group consisting of alkali metal hydrogen sulfate, oxalic acid, alkali metal dihydrogen phosphate, and nitric acid.

* * * * *